United States Patent
Ely et al.

(10) Patent No.: US 6,372,947 B1
(45) Date of Patent: Apr. 16, 2002

(54) PRODUCTION OF ALCOHOLATES

(75) Inventors: Wayne B. Ely, West Chester, PA (US); Carl Andrew Renner, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/769,622

(22) Filed: Jan. 23, 2001

(51) Int. Cl.⁷ .......................... C07C 31/30; C07C 29/00
(52) U.S. Cl. ......................................... 568/851; 568/840
(58) Field of Search ................................... 568/851, 840

(56) References Cited

U.S. PATENT DOCUMENTS

| | | | |
|---|---|---|---|
| 4,596,895 A | | 6/1986 | Auschner et al. |
| 4,857,665 A | * | 8/1989 | Hinrichs et al. ............ 568/851 |
| H1697 H | | 11/1997 | Tse |

FOREIGN PATENT DOCUMENTS

DD    118066    2/1976

OTHER PUBLICATIONS

Tse, US Statutory Invention Registration, Reg. No. H1697, 1997.*

* cited by examiner

Primary Examiner—Samuel Barts
Assistant Examiner—Elvis O. Price

(57) ABSTRACT

A process that can be used for producing an alkali metal alcoholate such as sodium alcoholate or for removing a residual mixture containing alkali metal and alkaline earth metal from a vessel such as, for example, a tank car or storage tank used in manufacturing an alkali metal is disclosed. The process comprises contacting a mixture, which comprises an alkali metal and an alkaline earth metal, with an alcohol under a condition sufficient to produce an alkali metal alcoholate and alkaline earth metal alcoholate and, optionally, separating and recovering the alkali metal alcoholate.

19 Claims, No Drawings

PRODUCTION OF ALCOHOLATES

FIELD OF THE INVENTION

This invention relates to a process for producing a solution of a metal alcoholate and to a process for removing alkali metal residues from a vessel used in the manufacture, storage and shipping of alkali metals.

BACKGROUND OF THE INVENTION

The alkali metals are very reactive metals and are not found in elemental form in nature. Electrolytic reduction is typically used to produce these metals. Sodium is by far the most commercially important of the alkali metals, and therefore the technology description is focussed on sodium. For many decades, the generally used process for making sodium has been the Downs electrolytic process. This process uses a molten salt electrolyte consisting of a mixture of NaCl, $CaCl_2$, and $BaCl_2$, and is operated at a high temperature of about 600° C.

Sodium metal electrolytically produced by this process contains small amounts of calcium metal co-deposited at the cathode because the decomposition potentials of the two metals are very close to one another. Elaborate and costly cooling, precipitation and/or filtration procedures are necessary to remove most of the calcium from sodium before the sodium is ready for shipment to customers. Typically the calcium so removed is in the form of a sodium/calcium filter-cake mixture, which is then purified by a high temperature recovery process.

In spite of these calcium removal steps, a small amount of calcium remains dissolved in the liquid sodium metal when it is transferred to a tank car or other vessel. Upon gradual cooling, more calcium eventually precipitates from the liquid sodium and settles to the bottom of the tank car as sludge containing a mixture of calcium, sodium and other impurities. After a number of tank car shipments, the sludge build-up becomes substantial and the sludge needs to be removed from the bottom of the tank car. Currently this is done by a cumbersome and fundamentally hazardous operation involving manual labor, jackhammers and the like to physically dig out the sludge. This labor-intensive operation is inherently hazardous because the sodium metal has a very low auto-ignition temperature in air of only about 120° C., and even at ambient temperatures can fire in the presence of water and air. This means that the manual removal of the accumulated sludge requires elaborate safety precautions, making this operation tedious, costly, and generally undesirable. The tank car sludge so removed is typically recycled back to the high temperature recovery process.

Purified alkali metal such as purified sodium is in the manufacture of alkali alcoholate such as, for example, sodium methylate. Sodium methylate is used widely as a reagent and catalyst for various chemical reactions. It is generally used as a solution in methanol for easy handling. Sodium methylate can be produced by batch reaction of sodium metal with methanol such as, for example, by adding bars, pieces, or molten sodium to an oxygen-reduced or removed, such as nitrogen-flushed, vessel operating at atmospheric pressure and containing an excess of methanol. It is based on the reaction $2Na+2CH_3OH \rightarrow 2NaOCH_3+H_2$. This reaction is highly exothermic, and reaction heat is typically removed by boiling off and refluxing methanol. The reaction is carefully controlled to avoid the entry of air into the vessel during the feeding of the sodium to avoid creating an explosive mixture. In large-scale production, by-product hydrogen and small amounts of nitrogen and methanol are usually vented to a flare for environmental emissions control.

Numerous efforts have been made to develop alternate processes to reduce the costs and hazards inherent in the above procedure. For example, East German Pat. No. 118,068 discloses a process for the continuous manufacture of sodium methylate using a sodium dispersion in an inert solvent to react with methanol. U.S. Pat. No. 4,596,895 discloses the reaction of methanol with a sodium amalgam manufactured by the once-important amalgam process as a means to produce sodium methylate. U.S. Statutory Invention Registration No. H1697 discloses a continuous process to make sodium methylate by feeding molten sodium and methanol to a stirred reactor under controlled conditions. These processes require the use of commercially pure sodium or sodium-mercury amalgam.

U.S. Pat. No. 4,857,665 discloses a process for converting the sodium contained in the residue accumulating in the filtration of liquid crude sodium from a fusion electrolysis process, and containing sodium, calcium, and their oxidation products, into a sodium alcoholate with a low content of sodium oxide, sodium hydroxide and sodium carbonate. This is done by heating the residue under intense mixing to temperatures in the range from 300° C. to 600° C. for 2 to 6 hours, adding the heat-treated residue to an alcohol, and separating the undesirable impurities by filtration. This process is costly to operate, and is not suitable for the removal of sodium sludge from tank cars and/or concomitant production of sodium methylate.

Therefore, there is a need to develop a process that can be used to produce an alkali metal alcoholate and can be safely and economically used for removing the sludge. The advantages of the invention include safer than the known process because it eliminates manual labor and personnel exposure for the clean-out operation; substituting the known "digging out" methods with a chemical dissolution process; producing a sodium methylate solution sodium/calcium sludge as a useful product; and cost-effective manner because no additional reactors, or agitators are required.

SUMMARY OF THE INVENTION

A process comprises contacting a mixture, which comprises an alkali metal and an alkaline earth metal, with an alcohol under a condition sufficient to produce an alkali metal alcoholate and alkaline earth metal alcoholate and, optionally, separating and recovering the alkali metal alcoholate.

DETAILED DESCRIPTION OF THE INVENTION

The process of the invention can be carried out in any suitable vessel, container, or reactor, known to one skilled in the art. The terms "vessel", "container", and "reactor" are interchangeable in this application and can refer to the tank car, storage tank, or other vessels used in the manufacture process of an alkali metal as discussed in the BACKGROUND OF THE INVENTION section. A suitable vessel is preferably equipped with a reflux condenser or other means of heat removal known to one skilled in the art to effect the production of an alkali metal alcoholate. The vessel can also be equipped with a piping system for the introduction of alcohol and an inert gas, and a venting system for the removal of the hydrogen produced. For example, a suitable vessel can be a sodium tank car or sodium storage tank equipped with heat removal equipment such as a reflux condenser.

The mixture can comprise an alkali metal and an alkaline earth metal, preferably about 65 to about 99 weight % alkali metal such as sodium and about 1 to about 35 weight % alkaline earth metal such as calcium. Preferably the mixture is a mixture of sodium and calcium obtained from the sludge deposited from molten sodium shipment or storage, or obtained during a sodium purification process (sodium/calcium filter cake), or a combination of these. Other impurities can also be present.

The preferred alcohol used to produce the alkali metal alcoholate is a substantially or essentially anhydrous liquid under ambient conditions. It can contain from 1 to about 10, preferably 1 to 4, carbon atoms. The presently preferred alcohol is methanol, ethanol, or combinations thereof. The most preferred alcohol is methanol.

Generally, it is preferred that a vessel containing the mixture is substantially or essentially free of oxygen. Oxygen can be substantially or essentially removed by flushing the vessel with an inert gas. The flushing can be done before, contemporaneously with, or after an alkali metal and an alkaline earth metal are introduced to the vessel. Examples of inert gases include nitrogen, argon, helium, or combinations of two or more thereof.

The process can be vigorous and exothermic. It is preferred to avoid introducing the alcohol to the vessel at a rate that generates heat faster than the heat can be removed. It is also preferred to avoid introducing the alcohol at a rate, which generates vapor from boiling the alcohol and from hydrogen formation, faster than the vapor handling capacity of the system thereby avoiding an excessive pressure in the system. Initially, until the temperature of the second mixture, as defined below, has risen to the reaction mass boiling point, alcohol should be introduced slowly, until the reaction proceeds as expected.

Accordingly an alcohol disclosed above is preferably slowly introduced to the mixture comprising the alkali metal and alkaline earth metal to form a second mixture while monitoring the hydrogen generation rate and the second mixture temperature. When the alkali metal and alkaline earth metal react with the alcohol, hydrogen is generated and temperature of the second mixture increases. It is desirable to control the alcohol feed rate so that it is limited by about the smaller of (i) the rate corresponding to the capacity of the heat removal means, or (ii) the rate corresponding to the vapor handling capacity of the venting system for the vessel. The term "slowly" used herein refers to a feed rate below the limits imposed by either (i) or (ii).

One skilled in the art can determine the rate corresponding to the heat removal capacity or to the vapor handling capacity in a variety of ways. For example, a simple trial of the process, while gradually increasing the feed rate of alcohol, can easily determine the rate at which some of the alcohol is not condensed and escapes the reflux condenser. The heat of reaction of the alcohol with the metals can be calculated and compared with the design capacity of the heat removal system. The temperature of the second mixture and/or that of the exit gas leaving the reflux condenser can be monitored to see if feed rates are exceeding heat removal capacity. If the reaction ceases for some unexpected reason, an undesirable excess of unreacted alcohol could accumulate and pose a risk of a too-vigorous reaction when the reaction resumed. Suitable allowance is therefore preferably made for the possibility that the mixture is not homogeneous, and that the reaction rate varies as the mixture is consumed.

Evaporation and refluxing of an alcohol such as methanol is a convenient way to remove the heat of reaction from the system, so that the temperature of the second mixture remains at the boiling point of the alcohol as influenced by the salt concentration of the solution. Other methods of heat removal can also be used, independently or in combination with refluxing. The conversion of alkali metal and alkaline earth metal to their corresponding alcoholates proceeds until all metal is consumed.

When the hydrogen generation rate drops to about zero, the introduction of alcohol is preferably discontinued to avoid unnecessary dilution of the alcoholates. The quantity of alcohol can be so determined. A sufficient time is allowed for the alcohol already in the second mixture to convert the alkali metal and alkaline earth metal to their alcoholates. This can be done at about 0° C. to the boiling point of the mixture, generally under atmospheric pressure for about 30 seconds to about 5 hours. Though an agitation means can be used, it generally does not require any mechanical agitation or recirculation equipment to effect complete and rapid reaction of the mixture such as the metal sludge with the alcohol.

The gases remaining after the reflux condenser consists of hydrogen and possibly inert gases and uncondensed alcohol and are preferably sent to a flare for treatment.

Thereafter, a product mixture comprising the alkali metal alcoholate, alkaline earth metal alcoholate, and excess alcohol is produced. The alkali metal alcoholate is generally substantially or essentially in solution whereas the alkaline earth metal alcoholate is substantially in solid form. The product mixture can be removed from the vessel by any means known to one skilled in the art such as, for example, pumping or blowing.

Optionally, the alkaline earth metal alcoholate is separated from the alcohol solution of alkali metal alcoholate and alcohol by any means known to one skilled in the art. Examples of suitable separation means includes filtration, centrifugation, sedimentation, or combinations or two or more thereof. Preferably this separation is done by sedimentation at a temperature of about 40° C. to about 60° C.

Alternatively the alkaline earth metal alcoholate can be removed from the solution and the resulting alcoholate solution either used as such or purified and concentration adjusted before use, depending on the particular applications.

An alkali metal methylate is readily alcohol-soluble, while an alkaline earth metal methylate is not. If the amount of alcohol fed is adequate to react with all alkali metal and alkaline earth metal, but inadequate to dissolve all alkali metal methylate formed, the reaction generally continues. The excess of alkali metal methylate above the solubility limit can form a bulk composition. For example, in experiments with sodium and methanol, this bulk composition is seen to reach as high as 60 weight percent sodium methylate. Such a composition can then be easily reacted to completion and adjusted to the desired strength by the addition of methanol. The ease of control of this process compares favorably with the continuous process for manufacture of sodium methylate as described in U.S. Statutory Invention Registration No. H1697 referenced above.

In a preferred embodiment, a process for producing sodium alcoholate can comprise, consist essentially, or consist of (a) flushing a vessel containing a first mixture, which comprises, consists essentially of, or consists of sodium and calcium, with an inert gas to remove air or oxygen; (b) slowly introducing an anhydrous alcohol to the vessel to form a second mixture, which comprises, consists essentially of, or consists of sodium, calcium, and alcohol, while monitoring the hydrogen gas generation rate and temperature of the vessel contents (second mixture); (c) when the evolution of hydrogen gas and temperature of the vessel contents show that the sodium/calcium is reacting with the alcohol, controlling the alcohol feed rate so that it is limited by about the smaller of (i) the rate corresponding to the capacity of the heat removal means of the vessel, or (ii) the rate corresponding to the vapor handling capacity of the venting system of the vessel; (d) when the hydrogen gas generation rate drops to about zero, discontinuing the introduction of alcohol; (e) holding the alcohol in contact with sodium/calcium for a sufficient time to convert sodium and calcium to sodium alcoholate and calcium alcoholate; (f) removing the sodium alcoholate, calcium alcoholate and any excess alcohol from the vessel; and, optionally, (g) separating the calcium alcoholate from the alcohol solution of sodium alcoholate by filtration, centrifugation or sedimentation. The reacting mixtures can comprise about 65 to about 99 weight % sodium and about 1 to about 35 weight % calcium, the range of compositions typically encountered in sodium manufacturing plants. Other impurities can also be present. Preferably the mixture of sodium and calcium used in the above process is obtained from the sludge deposited from molten sodium shipment or storage, or from a sodium/calcium mixture obtained during a sodium purification process, or a combination of these. The preferred alcohol is methanol. The vessel is equipped with a reflux condenser. Preferably the in step (g) separation is done by sedimentation at a temperature of about 40° C. to about 60° C.

The process of the present invention can also be used for removing residual mixtures containing alkali metal and alkaline earth metal from a vessel without the optional step disclosed above.

When the starting sludge is derived from sodium produced from a typical Downs process, as disclosed in the BACKGROUND OF THE INVENTION section, and the alcohol is methanol, the resulting sodium methylate solution can be suitable for selected applications without additional purification. The sodium methylate solution typically contains about 20% to 30% sodium methylate, with the balance methanol. The calcium content of this solution after solids separation is generally below the 400 ppm (parts per million by weight) Ca specification for typical industrial uses of sodium methylate.

The process of the invention is not only applicable to the clean out of alkali metal tank cars and other alkali metal containers, but it is also applicable to the conversion of many other sodium/calcium mixtures to sodium methylate solution. The industrial process can be carried out, for example, by adding this mixture to the tank car before starting the sludge cleaning operation, or by operating the process separately in a similarly equipped vessel.

The characteristics and conditions for the invention are described in the following illustrative examples. These examples should not be interpreted in any way as to limit the scope of the invention.

EXAMPLES

Example 1

The run was carried out inside a well-ventilated laboratory hood, and provisions were made for safe venting of the hydrogen gas that is released during the reaction. A quantity of approximately 50 grams of solidified sodium/calcium tank car sludge was placed in a 500 ml round bottom, three neck glass flask, fitted with a standard glass reflux condenser. An analysis of the heel material showed 97% sodium, 2% calcium, and 1% oxygen as oxides. After the flask was purged with nitrogen to remove air, methanol was introduced into the flask at ambient temperature at a rate of approximately 10 grams per minute to form a reaction mixture. The temperature of the reaction mixture rose until the boiling point of the reaction mixture was reached. A vigorous reaction occurred as the methanol reacted with the sodium sludge. The reaction continued until the sodium sludge was consumed and gas evolution ceased. At that point the whitish-gray reaction mass was subjected to sedimentation to separate the suspended fine particles of calcium methylate and other impurities from the sodium methylate solution. The sodium methylate concentration of the solution was 26% in methanol.

Example 2

This example shows that the reaction of methanol with the sodium/calcium mixture, as measured by the amount of hydrogen released, is dependent on the total amount of methanol fed, but not significantly dependent on the feed rate of methanol. A number of runs were conducted in which the rate of methanol was changed by a factor of five. Comparable data points are shown in the table below after 100 and 200 grams of methanol were fed. The runs were carried out under similar conditions as in Example 1, except typical sodium/calcium filter cake was used. An analysis of this filter cake showed the contents were 75% sodium, 21% calcium, and 4% oxygen in the form of oxides.

| Methanol feed, g/min | Total methanol fed, g | Hydrogen produced, g |
| --- | --- | --- |
| 2.3 | 100 | 0.82 |
| 2.3 | 200 | 1.54 |
| 5.9 | 100 | 0.82 |
| 5.9 | 200 | 1.51 |
| 5.9 | 100 | 0.77 |
| 5.9 | 200 | 1.42 |
| 10.6 | 100 | 0.71 |
| 10.6 | 200 | 1.28 |

The resultant solutions had sodium methylate concentrations of 20–30%, depending on when the alcohol feed was stopped.

These results clearly show that the total amount of methanol fed determined the degree of reaction. In similar runs, where the methanol feed was interrupted, the reaction ran to completion when feed flow was resumed similarly to the uninterrupted runs. This means that the process can easily be controlled by the amount of methanol fed, for example, to a tank car containing sodium filter cake and/or tank car heel material.

Example 3

This run was carried out in a manner similar to Example 1 using sodium filter cake, except that ethanol was used instead of methanol. The reaction proceeded similarly to when methanol was used, except that the initial reaction rate was slightly slower.

Example 4

In this example runs were carried out in a well-ventilated laboratory hood. Reaction mass from individual runs described in the previous examples was agitated and heated to a specified temperature. It was then transferred into a 100 ml graduated cylinder, located in a constant temperature bath at the same specified temperature, to a height of 124 mm. The height of the interface between clear solution and solution containing suspended solids was then recorded over time.

| | Temperature, ° C. | | | | |
|---|---|---|---|---|---|
| Time, minutes | 22 | 40 | 50 | 60 | 70 |
| 0 | 124 | 124 | 124 | 124 | 124 |
| 60 | 116 | 66 | 72 | 66 | 94 |
| 120 | 110 | 62 | 55 | 58 | 66 |

This sample shows the benefit of elevated temperature during the solids separation step of the settling rate for solutions at elevated temperatures was considerably faster than for solution held at 22° C. This surprising result exceeds the increase expected from changes in viscosity and density of solutions at different temperatures. The results show that the most preferred solids separation is about 40° C. to about 60° C.

What is claimed is:

1. A process comprising adding an alcohol to a mixture, which comprises an alkali metal and an alkaline earth metal, under a condition sufficient to produce an alkali metal alcoholate and alkaline earth metal alcoholate, wherein said mixture comprises about 65 to about 99 weight % alkali metal and about 1 to 35 weight % alkaline earth metal and, alcohol is combined with said mixture in such a rate that is limited by the smaller of (i) the rate corresponding to the capacity of heat removal means, or (ii) the rate and, optionally, separating and recovering said alkali metal alcoholate.

2. A process according to claim 1 wherein said alkali metal is sodium and said alkaline earth metal is calcium.

3. A process according to claim 1 wherein said alcohol has 1 to about 4 carbon atoms per molecule.

4. A process according to claim 2 wherein said alcohol is ethanol, methanol, or combinations thereof.

5. A process according to claim 4 wherein said alcohol is methanol.

6. A process according to claim 5 wherein said process is carried out in a vessel containing said mixture and alcohol is introduced to said vessel.

7. A process comprising adding an alcohol in a vessel to a mixture under a condition sufficient to produce an alkali metal alcoholate and alkaline earth metal alcoholate wherein
said mixture comprises about 65 to about 99 weight % alkali metal and about 1 to about 35 weight % alkaline earth metal;
said alcohol contains 1 to about 4 carbon atoms per molecule;
said vessel is equipped with a heat removal means; and
said process comprises (1) flushing said vessel with an inert gas to remove air or oxygen; (2) introducing said alcohol to said vessel at a rate limited by about the smaller of (i) the rate corresponding to the capacity of the heat removal equipment, or (ii) the rate corresponding to the vapor handling capacity of the system; (3) discontinuing said alcohol when there is substantially no hydrogen generation; (4) allowing for a sufficient time to convert said alkali metal and alkaline earth metal to their corresponding alcoholates; (5) removing said alkali metal alcoholate and alkaline earth metal alcoholate from said vessel; and, optionally (6) separating said alkaline earth metal alcoholate from said alkali metal alcoholate.

8. A process according to claim 7 wherein said alkali metal is sodium and said alkaline earth metal is calcium.

9. A process according to claim 7 wherein said alcohol is ethanol, methanol, or combinations thereof.

10. A process according to claim 8 wherein said alcohol is methanol.

11. A process according to claim 7 wherein said alkali metal is sodium and said alkaline earth metal is calcium; said alcohol is ethanol, methanol, or combinations thereof; and said heat removal means is a reflux condenser.

12. A process according to claim 11 wherein said vessel is a tank car or storage tank used in manufacturing said alkali metal.

13. A process according to claim 1 wherein separation is carried out at about 40° C. to about 60° C.

14. A process according to claim 7 wherein separation is carried out at about 40° C. to about 60° C.

15. A process according to claim 12 wherein separation is carried out at about 40° C. to about 60° C.

16. A process according to claim 12 wherein said mixture is introduced to said vessel before, contemporaneously with, or after introducing said alcohol.

17. A process according to claim 12 wherein said mixture is tank car sludge.

18. A process for producing sodium alcoholate comprising (a) flushing a vessel containing a reaction mixture with nitrogen to remove air or oxygen wherein said mixture comprises about 65 to about 99 weight % sodium and about 1 to about 35 weight % calcium; (b) slowly introducing methanol to said vessel containing said mixture; (c) controlling the methanol feed rate so that said rate is limited by about the smaller of (i) the rate corresponding to the capacity of the heat removal equipment of said vessel or (ii) the rate corresponding to the vapor handling capacity of the venting system of said vessel; (d) when the hydrogen gas generation rate drops to about zero, discontinuing said introducing methanol; (e) converting said sodium and calcium to sodium alcoholate and calcium alcoholate; (f) removing said sodium alcoholate and calcium alcoholate from said vessel; and, optionally, (g) separating said calcium alcoholate from said sodium alcoholate.

19. A process according to claim 18 wherein said process is carried out without agitation.

* * * * *